United States Patent
Hölscher et al.

(10) Patent No.: US 10,920,169 B2
(45) Date of Patent: Feb. 16, 2021

(54) AMBERGRIS AND/OR INDOLE-LIKE COMPOSITIONS OF ODORIFEROUS SUBSTANCES

(71) Applicant: SYMRISE AG, Holzminden (DE)

(72) Inventors: Bernd Hölscher, Halle (DE); Johannes Panten, Höxter (DE)

(73) Assignee: SYMRISE AG, Holzminden (DE)

( * ) Notice: Subject to any disclaimer, the term of this patent is extended or adjusted under 35 U.S.C. 154(b) by 0 days.

(21) Appl. No.: 16/623,854

(22) PCT Filed: Jun. 19, 2017

(86) PCT No.: PCT/EP2017/064939
§ 371 (c)(1),
(2) Date: Dec. 18, 2019

(87) PCT Pub. No.: WO2018/233804
PCT Pub. Date: Dec. 27, 2018

(65) Prior Publication Data
US 2020/0148974 A1    May 14, 2020

(51) Int. Cl.
| | |
|---|---|
| *A61K 8/00* | (2006.01) |
| *A61K 8/18* | (2006.01) |
| *A61Q 13/00* | (2006.01) |
| *C11B 9/00* | (2006.01) |
| *A61K 8/33* | (2006.01) |
| *A61K 8/34* | (2006.01) |

(52) U.S. Cl.
CPC .............. *C11B 9/0034* (2013.01); *A61K 8/33* (2013.01); *A61K 8/34* (2013.01); *A61Q 13/00* (2013.01)

(58) Field of Classification Search
CPC ........... C11B 9/0034; A61K 8/33; A61K 8/34; A61Q 13/00
USPC ............................................ 512/23, 22, 8, 1
See application file for complete search history.

(56) References Cited

U.S. PATENT DOCUMENTS

2012/0121737 A1* 5/2012 Vielhaber ............ A61K 31/045
                                                              424/737
2014/0323375 A1* 10/2014 Bauer .................... C11D 3/507
                                                              510/101

FOREIGN PATENT DOCUMENTS

| CA | 2281521 A1 | 8/1998 |
| WO | 9955811 A1 | 11/1999 |
| WO | 0214253 A1 | 2/2002 |

OTHER PUBLICATIONS

International Search Report and Written Opinion dated Oct. 16, 2017 for corresponding PCT Application No. PCT/EP2017/064939.

* cited by examiner

*Primary Examiner* — Jessica Whiteley
(74) *Attorney, Agent, or Firm* — Polsinelli PC

(57) ABSTRACT

The present invention primarily relates to the use of one or more compound(s) of formula (I)

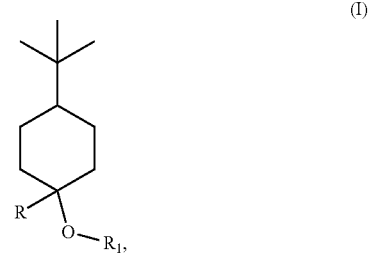

(I)

as fragrance, wherein R is methyl or ethyl and $R_1$ is H, methyl or ethyl. The invention further relates to new fragrance compositions comprising one or more compound(s) of formula (I), as described herein, the use of said fragrance compositions, perfumed articles comprising said fragrance compositions, and various methods of perfuming said articles or for imparting, modifying and/or enhancing certain olfactory notes.

23 Claims, No Drawings

AMBERGRIS AND/OR INDOLE-LIKE COMPOSITIONS OF ODORIFEROUS SUBSTANCES

CROSS-REFERENCE TO RELATED APPLICATIONS

This application is a national stage application (under 35 U.S.C. § 371) of PCT/EP2017/064939, filed Jun. 19, 2017, which is incorporated herein by reference in its entirety.

The present invention primarily relates to the use of one or more compound(s) of formula (I), as described herein, as fragrance. The invention further relates to new fragrance compositions comprising one or more compound(s) of formula (I), as described herein, the use of said fragrance compositions, perfumed articles comprising said fragrance compositions, and various methods of perfuming said articles or for imparting, modifying and/or enhancing certain olfactory notes.

Further aspects and preferred forms of the present invention result from the following explanations, the attached examples and in particular the attached patent claims.

In the perfume industry, a multitude of different compounds are known which are used to convey a fragrance. However, there is a constant need for novel advantageous compounds which, in addition to their positive and original olfactory properties, have additional positive secondary properties.

During the search for suitable compounds, the skilled person is faced with the difficult task of either identifying suitable fragrances from a very large number of known compounds or of producing new compounds with the desired properties. It is thereby not possible to predict whether new compounds will have an odour at all and whether this odour will have desirable or undesirable olfactory properties. When finding a compound with a positive odour, it is also very questionable what odour it is and to what extent the compound also has positive secondary properties.

Many fragrances known so far have some clear disadvantages. For example, they often have a very limited stability and extensiveness, low adhesion properties, low radiance, poor solubility and often have to be used in high dosages.

In addition, very high demands are placed on new fragrances. For example, they should have a very good biodegradability and be dermatologically and toxicologically harmless.

The odour "ambergris" represents one of the highly preferred olfactory notes in perfumes. It gives perfumes a special exclusivity and luxuriousness. Originally, ambergris was extracted from the digestive tract of sperm whales; today, ambergris scents from other sources are preferred. The disadvantage of many ambergris fragrances is that their olfactory impression is only gradually perceived, which is why it is particularly difficult to represent the ambergris odour in the top note of a perfume.

Indole-like scents are often used in perfumes and are among the very popular olfactory notes to impart a special floral radiance to the perfume. Ambergris notes, which also have an indole odour, are perceived as being of particularly high quality.

The object of the present invention was to provide compounds which do not exhibit or which mitigate the disadvantages of the state of the art mentioned above. In particular, the object of the invention was to provide fragrances which can impart, modify and/or enhance the olfactory notes(s) ambergris and/or indole-like and which also have positive secondary properties, such as for example good biodegradability and/or high dermatological compatibility.

The object is solved according to the invention by the use of one or more compound(s) of formula (I)

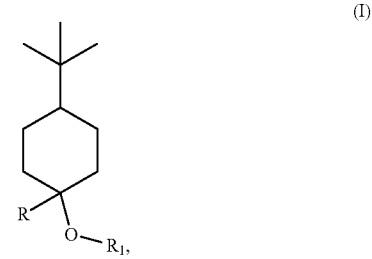

as a fragrance, wherein R is methyl or ethyl and $R_1$ is H, methyl or ethyl.

A compound of formula (I) to be used according to the invention may be present in any stereoisomeric form. In the context of the present invention, any mixtures of stereoisomers of the compound(s) of formula (I) may also be used, for example a mixture of diastereoisomers, a mixture of enantiomers or a racemate, i.e. the term "compound(s) of formula (I)" in the context of this text also includes the said any mixtures of different stereoisomers of the compound(s) of formula (I).

What is stated herein for a compound of formula (I), in particular the advantages described herein, also apply to a mixture of stereoisomers of the compound(s) of formula (I) to be used or applied according to the invention.

If, in the context of this text, a discrepancy should occur by mistake between the chemical name and the structural formulas shown, the structural formula shown shall apply.

Surprisingly, it was found that the compounds of formula (I) to be used according to the invention have an ambergris- and/or indole-like olfactory note. Furthermore, they exhibit a high stability and extensiveness, good adhesion properties, a very high radiance, a low odour threshold, a very good solubility and miscibility, a low tendency to react with other fragrances, a very good dermatological and toxicological compatibility as well as a good biodegradability.

A further advantage of the compounds of formula (I) to be used according to the invention is their high scent intensity at a comparatively low dosage. This is of particular interest in terms of environmental pollution control, as the amount of substances released into the environment can thereby be kept to a minimum. Furthermore, the ambergris note is perceived particularly quickly, so that the compounds of formula (I) are suitable for example as a top note in a perfume oil.

The compounds of formula (I) themselves are very stable and also exhibit high stability under unfavourable conditions, e.g. high oxygen content, high content of oxidizing agents or reducing agents and high pH values.

Preferred is a use according to the invention, wherein one, several or all of the compound(s) of formula (I) is or are selected from the group consisting of compounds of formula (Ia), compounds of formula (Ib) and compounds of formula (Ic)

(Ia)
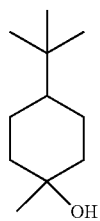

(Ib)
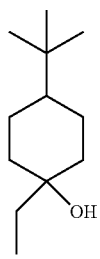

(Ic)
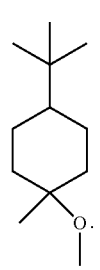

The compounds of formula (Ia), (Ib) and (Ic) are characterized by having a particularly complex, radiant and highly intense ambergris scent, even at low dosages. In addition, they have an indole-like scent, so that the particularly desired combination of ambergris with flowery radiance is created. The following overview depicts the olfactory properties of the compounds of formula (Ia), (Ib) and (Ic) to be preferably used according to the invention:

| Compound | Molecular weight | Structure | Odour |
|---|---|---|---|
| (Ia) | 170 | 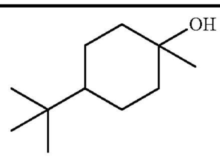 | ambergris, indole-like, animalistic, civet ambrinol-like |
| (Ib) | 184 | 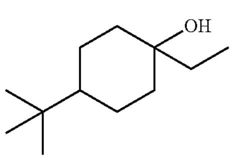 | ambergris, indole-like, animalistic, earthy |
| (Ic) | 184 | 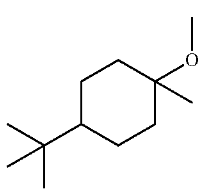 | ambergris, indole-like, animalistic, erogenous |

Preferably, the use according to the invention therefore relates to a use of one or more compound(s) of formula (I), preferably one or more compound(s) of formula (I) selected from the group consisting of the compounds of formula (Ia), compounds of formula (Ib) and compounds of formula (Ic), for imparting, modifying and/or enhancing one or more olfactory notes selected from the group consisting of ambergris, indole and woody, preferably for rounding off, harmonizing and/or improving the natural olfactory impression of one or more further fragrance(s) and/or for imparting, modifying and/or enhancing an ambergris-like and/or woody and/or indol-like olfactory top note.

Another aspect of the present invention relates to a fragrance composition comprising or consisting of one or more compound(s) of formula (I)

(I)
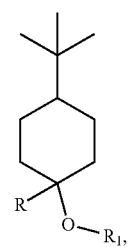

wherein R is methyl or ethyl and $R_1$ is H, methyl or ethyl, preferably comprising or consisting of one or more compound(s) of formula (Ia) and/or (Ib) and/or (Ic), (Ia)
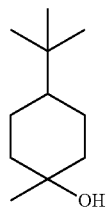

(Ib)
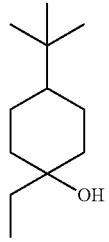

(Ic)
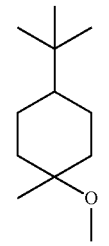

and
one or more solvent(s), wherein preferably the one, several or all of the solvent(s) is/are selected from the group consisting of ethanol, isopropanol, diethylene glycol monoethyl ether, glycerol, propylene glycol, 1,2-butylene glycol, dipropylene glycol, diethyl phthalate, triethyl citrate and isopropyl myristate, and/or one or more further fragrance(s), wherein preferably the ratio of the total mass of the compound(s) of formula (I) in the fragrance mixture to the total mass of further fragrance(s) in the fragrance mixture, if present, is 1:999 to 999:1, preferably 1:99 to 1:1, more preferably 1:99 to 1:2, further preferably 1:90 to 1:5 and especially preferably 1:80 to 1:10.

The use of the above-mentioned solvents is particularly advantageous, since the compound(s) of formula (I) to be used according to the invention is (are) particularly well able to dissolve themselves in these solvents.

It is also advantageous that the compound(s) of formula (I) to be used according to the invention is/are particularly well soluble in other fragrances in a very broad concentration ratio and has/have low reactivity with other fragrances. The compounds of formula (I), as defined above, round off the odour in fragrance compositions containing one or more further fragrance(s), have a harmonizing effect and improve the natural olfactory impression of the fragrance composition in general.

Examples of further fragrances with which the compounds of formula (I) to be used according to the invention can be advantageously combined can be found, for example, in "S. Arctander, Perfume and Flavor Chemicals, Vol. I and II, Montclair, N.J., 1969, author's edition" or "H. Surburg and J. Panten, Common Fragrance and Flavor Materials, 5th ed., Wiley-VCH, Weinheim, 2006". In detail are to be mentioned:

Extracts from natural raw materials such as essential oils, concretes, absolues, resins, resinoids, balsams, tinctures such as for example ambergris tincture; amyris oil; angelica seed oil; angelica root oil; anise oil; valerian oil; basil oil; tree moss absolute; bay oil; mugwort oil; benzoe resin; bergamot oil; beeswax absolue; birch tar oil; bitter almond oil; savory oil; bucco leaf oil; cabreuva oil; cade oil; calmus oil; camphor oil; cananga oil; cardamom oil; cascarilla oil; cassia oil; cassie absolue; castoreum absolue; cedar leaf oil; cedar wood oil; cistus oil; citronella oil; lemon oil; copaiba balsam; copaiba balsam oil; coriander oil; costus root oil; cumin oil; cypress oil; davana oil; dill herb oil; dill seed oil; eau de brouts absolue; oak moss absolue; elemi oil; tarragon oil; eucalyptus citriodora oil; eucalyptus oil; fennel oil; spruce needle oil; galbanum oil; galbanum resin; geranium oil; grapefruit oil; guaiac wood oil; gurjun balsam; gurjun balsam oil; helichrysum absolue; helichrysum oil; ginger oil; iris root absolue; iris root oil; jasmine absolue; calamus oil; chamomile oil blue; roman chamomile oil; carrot seed oil; cascarilla oil; pine needle oil; spearmint oil; caraway oil; labdanum oil; labdanum absolue; labdanum resin; lavandin absolue; lavandin oil; lavender absolue; lavender oil; lemongrass oil; lovage oil; distilled lime oil; pressed lime oil; linaloe oil; litsea cubeba oil; laurel leaf oil; macis oil; marjoram oil; mandarin oil; massoi bark oil; mimosa absolue; musk seed oil; musk tincture; muscat sage oil; nutmeg oil; myrrh absolue; myrrh oil; myrtle oil; clove leaf oil; clove blossom oil; neroli oil; olibanum absolue; olibanum oil; opopanax oil; orange blossom absolue; orange oil; origanum oil; palmarosa oil; patchouli oil; perilla oil; peru balsam oil; parsley leaf oil; parsley seed oil; petite grain oil; peppermint oil; pepper oil; pimento oil; pine oil; poley oil; rose absolue; rosewood oil; rose oil; rosemary oil; dalmatian sage oil; spanish sage oil; sandalwood oil; celery seed oil; spiked lavender oil; star anise oil; styrax oil; marigold oil; fir needle oil; tea tree oil; turpentine oil; thyme oil; tolu balsam; tonka absolue; tuberose absolue; vanilla extract; violet leaf absolue; verbena oil; vetiver oil; juniper berry oil; wine yeast oil; wormwood oil; wintergreen oil; ylang oil; ysop oil; civet absolue; cinnamon leaf oil; cinnamon bark oil and fractions thereof, or ingredients isolated therefrom;

Single fragrances from the group of hydrocarbons, such as e.g. 3-carene; α-pinene; β-pinene; α-terpinene; γ-terpinene; p-cymol; bisabolene; camphene; caryophyllene; cedrene; farnesene; limonene; longifolene; myrcene; ocimene; valencene; (E,Z)-1,3,5-undecatriene; styrene; diphenylmethane;

of aliphatic alcohols, such as e.g. hexanol; octanol; 3-octanol; 2,6-dimethylheptanol; 2-methyl-2-heptanol; 2-methyl-2-octanol; (E)-2-hexenol; (E)- and (Z)-3-hexenol; 1-octene-3-ol; a mixture of 3,4,5,6,6-pentamethyl-3/4-hepten-2-ol and 3,5,6,6-tetramethyl-4-methyleneheptan-2-ol; (E,Z)-2,6-nonadienol; 3,7-dimethyl-7-methoxyoctan-2-ol; 9-decenol; 10-undecenol; 4-methyl-3-decen-5-ol;

of aliphatic aldehydes and their acetals, such as e.g. hexanal; heptanal; octanal; nonanal; decanal; undecanal; dodecanal; tridecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-9-undecenal; 2,6,10-trimethyl-5,9-undecadienal; heptanal diethylacetal; 1,1-dimethoxy-2,2,5-trimethyl-4-hexene; citronellyl oxyacetaldehyde; 1-(1-methoxy-propoxy)-(E/Z)-3-hexene;

of aliphatic ketones and their oximes such as e.g. 2-heptanone; 2-octanone; 3-octanone; 2-nonanone; 5-methyl-3-heptanone; 5-methyl-3-heptanone oxime; 2,4,4,7-tetramethyl-6-octen-3-one; 6-methyl-5-hepten-2-one;

of aliphatic sulphur-containing compounds such as e.g. 3-methylthiohexanol; 3-methylthiohexyl acetate; 3-mercaptohexanol; 3-mercaptohexyl acetate; 3-mercaptohexyl butyrate; 3-acetylthiohexyl acetate; 1-menthene-8-thiol;

of aliphatic nitriles such as e.g. 2-nonic acid nitrile; 2-undecenoic acid nitrile; 2-tridecenoic acid nitrile; 3,12-tridecadienoic acid nitrile; 3,7-dimethyl-2,6-octadienoic acid nitrile; 3,7-dimethyl-6-octenoic acid nitrile;

of esters of aliphatic carboxylic acids, such as e.g. (E)- and (Z)-3-hexenyl formate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octene-3-yl acetate; ethyl butyrate; butyl butyrate; isoamyl butyrate; hexyl butyrate; (E)- and (Z)-3-hexenyl isobutyrate; hexyl crotonate; ethyl isovalerate; ethyl 2-methyl pentanoate; ethyl hexanoate; allyl hexanoate; ethyl heptanoate; allyl heptanoate; ethyl octanoate; ethyl-(E,Z)-2,4-decadienoate; methyl-2-octinate; methyl-2-noninate; allyl-2-isoamyloxyacetate; methyl-3,7-dimethyl-2,6-octadienoate; 4-methyl-2-pentyl crotonate;

of acyclic terpene alcohols such as e.g. citronellol; geraniol; nerol; linalool; lavadulol; nerolidol; farnesol; tetrahydrolinalool; tetrahydrogeraniol; 2,6-dimethyl-7-octen-2-ol; 2,6-dimethyloctan-2-ol; 2-methyl-6-methylen-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol 2,6-dimethyl-2,5,7-octatrien-1-ol; and their formates, acetates, propionates, isobutyrates, butyrates, isovalerates, pentanoates, hexanoates, crotonates, tiglinates and 3-methyl-2-butenoates;

of acyclic terpene aldehydes and ketones such as e.g. geranial; neral; citronellal; 7-hydroxy-3,7-dimethyloctanal; 7-methoxy-3,7-dimethyloctanal; 2,6,10-trimethyl-9-undecenal; geranylacetone; as well as the dimethyl and diethyl acetals of geranial, neral, 7-hydroxy-3,7-dimethyloctanal;

of cyclic terpene alcohols, such as e.g. menthol; isopulegol; alpha-terpineol; terpinenol-4; menthan-8-ol; menthan-1-ol; menthan-7-ol; borneol; isoborneol; linalool oxide; nopol; cedrol; ambrinol, vetiverol; guaiol; and their formates, acetates, propionates, isobutyrates, butyrates, isovalerates, pentanoates, hexanoates, crotonates, tiglinates and 3-methyl-2-butenoates;

of cyclic terpene aldehydes and ketones such as e.g. menthone; isomenthone; 8-mercaptomenthan-3-one; carvone; camphor; fenchone; alpha-ionone; beta-ionone; alpha-n-methylionone; beta-n-methylionone; alpha-isomethylionone; beta-isomethylionone; alpha-irone; alpha-damascone; beta-damascone; beta-damascenone; delta-damascone; gamma-damascone; 1-(2,4,4-trimethyl-2-cyclohexen-1-yl)-2-buten-1-one; 1,3,4,6,7,8a-Hexahydro-1,1,5,5-tetramethyl-2H-2,4a-methanonaphthalen-8(5H)-one;2-methyl-4-(2,6,6-trimethyl-1-cyclohexen-1-yl)-2-butenal; nootkatone; di hydronootkatone; 4,6,8-megastigmatrien-3-one; alpha-sinensal; beta-sinensal; acetylated cedarwood oil (methyl cedryl ketone);

of cyclic alcohols such as e.g. 4-tert.-butylcyclohexanol; 3,3,5-trimethylcyclohexanol; 3-isocamphylcyclohexanol; 2,6,9-trimethyl-Z2,Z5, E9-cyclododecatrien-1-ol; 2-isobutyl-4-methyltetrahydro-2H-pyran-4-ol;

of cycloaliphatic alcohols, such as e.g. alpha,3,3-trimethylcyclohexylmethanol; 1-(4-isopropylcyclohexyethanol; 2-methyl-4-(2,2,3-trimethyl-3-cyclopent-1-yl)butanol; 2-methyl-4-(2,2,3-trimethyl-3-cyclopent-1-yl)-2-buten-1-ol; 2-ethyl-4-(2,2,3-trimethyl-3-cyclopent-1-yl)-2-buten-1-ol; 3-methyl-5-(2,2,3-trimethyl-3-cyclopent-1-yl)-pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-tri methylcyclohexyl)pentan-3-ol; 1-(2,2,6-trimethylcyclohexyl)hexan-3-ol;

of cyclic and cycloaliphatic ethers such as e.g. cineol; cedryl methyl ether; cyclododecyl methyl ether; 1,1-dimethoxycyclododecane; (ethoxymethoxy)cyclododecane; alpha-cedrene epoxide; 3a,6,6,9a-tetramethyldodecahydronaphtho[2,1-b]furan; 3a-ethyl-6,6,9a-trimethyldodecahydronaphtho[2,1-b]furan; 1,5,9-trimethyl-13-oxabicyclo[10.1.0]trideca-4,8-diene; rose oxide; 2-(2,4-dimethyl-3-cyclohexen-1-yl)-5-methyl-5-(1-methylpropyl)-1,3-dioxane;

of cyclic and macrocyclic ketones such as e.g. 4-tert.-butylcyclohexanone; 2,2,5-trimethyl-5-pentylcyclopentanone; 2-heptylcyclopentanone; 2-pentylcyclopentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopentadecenone; 3-methyl-5-cyclopentadecenone; 3-methylcyclopentadecanone; 4-(1-ethoxyvinyl)-3,3,5,5-tetramethylcyclohexanone; 4-tert.-pentylcyclohexanone; 5-cyclohexadecen-1-one; 6,7-dihydro-1,1,2,3,3-pentamethyl-4(5H)-indanone; 8-cyclohexadecen-1-one; 9-cycloheptadecen-1-one; cyclopentadecanone; cyclohexadecanone;

of cycloaliphatic aldehydes such as e.g. 2,4-dimethyl-3-cyclohexene carbaldehyde; 2-methyl-4-(2,2,6-trimethyl-cyclohexen-1-yl)-2-butenal; 4-(4-hydroxy-4-methylpentyl)-3-cyclohexene carbaldehyde; 4-(4-methyl-3-penten-1-yl)-3-cyclohexene carbaldehyde;

of cycloaliphatic ketones such as e.g. 1-(3,3-dimethylcyclohexyl)-4-penten-1-one; 2,2-dimethyl-1-(2,4-dimethyl-3-cyclohexen-1-yl)-1-propanone; 1-(5,5-dimethyl-1-cyclohexen-1-yl)-4-penten-1-one; 2,3,8,8-tetramethyl-1,2,3,4,5,6,7,8-octahydro-2-naphtalenylmethylketone; methyl-2,6,10-trimethyl-2,5,9-cyclododecatrienylketone; tert.-butyl-(2,4-dimethyl-3-cyclohexen-1-yl)ketone;

of the esters of cyclic alcohols, such as e.g. 2-tert-butylcyclohexyl acetate; 4-tert-butylcyclohexyl acetate; 2-tert-pentylcyclohexyl acetate; 4-tert-pentylcyclohexyl acetate; 3,3,5-trimethylcyclohexyl acetate; decahydro-2-naphthyl acetate; 2-cyclopentyl cyclopentyl crotonate; 3-pentyltetrahydro-2H-pyran-4-yl acetate; decahydro-2,5,5,8a-tetramethyl-2-naphthyl acetate; 4,7-methano-3a,4,5,6,7,7a-hexahydro-5 or 6-indenyl acetate; 4,7-methano-3a,4,5,6,7,7a-hexahydro-5, or 6-indenyl propionate; 4,7-methano-3a,4,5,6,7,7a-hexahydro-5, or 6-indenyl isobutyrate; 4,7-methanooctahydro-5, or 6-indenyl acetate;

of esters of cycloaliphatic alcohols such as 1-cyclohexylethylcrotonate;

of esters of cycloaliphatic carboxylic acids, such as e.g. allyl-3-cyclohexylpropionate; allyl cyclohexyl oxyacetate; cis- and trans-methyldihydrojasmonate; cis- and trans-methyljasmonate; methyl-2-hexyl-3-oxocyclopentane carboxylate; ethyl-2-ethyl-6,6-dimethyl-2-cyclohexene carboxylate; ethyl-2,3,6,6-tetramethyl-2-cyclohexene carboxylate; ethyl-2-methyl-1,3-dioxolane-2-acetate;

of araliphatic alcohols, such as e.g. benzyl alcohol; 1-phenylethyl alcohol; 2-phenylethyl alcohol; 3-phenylpropanol; 2-phenylpropanol; 2-phenoxyethanol; 2,2-dimethyl-3-phenyl propanol; 2,2-dimethyl-3-(3-methylphenyl)propanol; 1,1-dimethyl-2-phenylethyl alcohol; 1,1-dimethyl-3-phenylpropanol; 1-ethyl-1-methyl-3-phenylpropanol; 2-methyl-5-phenylpentanol; 3-methyl-5-phenylpentanol; 3-phenyl-2-propen-1-ol; 4-methoxybenzyl alcohol; 1-(4-isopropylphenyl)ethanol;

of esters of araliphatic alcohols and aliphatic carboxylic acids, e.g. benzyl acetate; benzyl propionate; benzyl isobutyrate; benzyl isovalerate; 2-phenylethyl acetate; 2-phenylethyl propionate; 2-phenylethyl isobutyrate; 2-phenylethyl isovalerate; 1-phenylethyl acetate; alpha-trichloromethylbenzyl acetate; alpha,alpha-dimethylphenylethyl acetate; alpha,alpha-dimethylphenylethyl butyrate; cinnamyl acetate; 2-phenoxyethylisobutyrate; 4-methoxybenzylacetate;

of araliphatic ethers such as e.g. 2-phenylethylmethylether; 2-phenylethylisoamylether; 2-phenylethyl-1-ethoxyethylether; phenylacetaldehyde dimethylacetal; phenylacetaldehyde diethylacetal; hydratropaaldehyde dimethylacetal; phenylacetaldehyde glycerol acetal; 2,4,6-trimethyl-4-phenyl-1,3-dioxane; 4,4a,5,9b-tetrahydroindeno[1,2-d]-m-dioxin; 4,4a,5,9b-tetrahydro-2,4-dimethylindeno[1,2-d]-m-dioxin;

of aromatic and araliphatic aldehydes such as e.g. benzaldehyde; phenylacetaldehyde; 3-phenylpropanal; hydratropaaldehyde; 4-methylbenzaldehyde; 3-(4-ethylphenyl)-2,2-dimethylpropanal; 2-methyl-3-(4-isopropylphenyl)propanal; 2-methyl-3-(4-tert.-butylphenyl)propanal; 3-(4-tert-butylphenyl)propanal; 2-methyl-3-(4-isopropylphenyl)propanal; 3-(4-tert.-butylphenyl)propanal; cinnamic aldehyde; alpha-butyl cinnamic aldehyde; alpha-amyl cinnamic aldehyde; alpha-hexyl cinnamic aldehyde; 3-methyl-5-phenylpentanal; 4-methoxybenzaldehyde; 4-hydroxy-3-methoxybenzaldehyde; 4-hydroxy-3-ethoxybenzaldehyde; 3,4-methylenedioxybenzaldehyde; 3,4-dimethoxybenzaldehyde; 2-methyl-3-(4-methoxyphenyl)propanal; 2-methyl-3-(4-methylenedioxyphenyl)propanal;

of aromatic and araliphatic ketones such as e.g. acetophenone; 4-methylacetophenone; 4-methoxyacetophenone; 4-tert.-butyl-2,6-dimethylacetophenone; 4-phenyl-2-butanone; 4-(4-hydroxyphenyl)-2-butanone;1-(2-naphthalenyl)ethanone; 2-benzofuranylethanone; (3-methyl-2-benzofuranyl)ethanone; benzophenone; 1,1,2,3,3,6-hexamethyl-5-indanylmethylketone; 6-tert.-butyl-1,1-dimethyl-4- indanylmethylketone; 1-[2,3-dihydro-1,1,2,6-tetramethyl-3-(1-methylethyl)-1H-5-indenyl]ethanone; 5',6',7',8'-tetrahydro-3',5',5',6',8',8'-hexamethyl-2-acetonaphthone;

of aromatic and araliphatic carboxylic acids and their esters, such as e.g. benzoic acid; phenylacetic acid; methyl benzoate; ethyl benzoate; hexyl benzoate; benzyl benzoate; methyl phenyl acetate; ethyl phenyl acetate; geranyl phenyl acetate; phenylethyl phenyl acetate; methyl cinnamate; ethyl cinnamate; benzyl cinnamate; phenylethyl cinnamate; cinnamyl cinnamate; allylphenoxyacetate; methyl salicylate; isoamyl salicylate; hexyl salicylate; cyclohexyl salicylate; cis-3-hexenyl salicylate; benzyl salicylate; phenylethyl salicylate; methyl-2,4-dihydroxy-3,6-dimethylbenzoate; ethyl-3-phenylglycidate; ethyl-3-methyl-3-phenylglycidate;

of nitrogen-containing aromatic compounds such as e.g. 2,4,6-trinitro-1,3-dimethyl-5-tert.-butylbenzene; 3,5-dinitro-2,6-dimethyl-4-tert.-butylacetophenone; cinnamic acid nitrile; 3-methyl-5-phenyl-2-pentenoic acid nitrile; 3-methyl-5-phenylpentanoic acid nitrile; methylanthranilate; methy-N-methylanthranilate; Schiff bases of methylanthranilate with 7-hydroxy-3,7-dimethyloctanal, 2-methyl-3-(4-tert.-butylphenyl)propanal or 2,4-dimethyl-3-cyclohexene carbaldehyde; 6-isopropylquinoline; 6-isobutylquinoline; 6-sec.-butylquinoline; 2-(3-phenylpropyl)pyridine; indole; skatole; 2-methoxy-3-isopropylpyrazine; 2-isobutyl-3-methoxypyrazine;

of phenols, phenylethers and phenyl esters, such as e.g. estragol; anethole; eugenol; eugenyl methyl ether; isoeugenol; isoeugenyl methyl ether; thymol; carvacrol; diphenyl ether; beta-naphthyl methyl ether; beta-naphthyl ethyl ether; beta-naphthylisobutyl ether; 1,4-dimethoxybenzene; eugenyl acetate; 2-methoxy-4-methylphenol; 2-ethoxy-5-(1-propenyl)phenol; p-cresylphenyl acetate;

of heterocyclic compounds such as e.g. 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one;

of lactones such as 1,4-octanolide; 3-methyl-1,4-octanolide; 1,4-nonanolide; 1,4-decanolide; 8-decen-1,4-olide; 1,4-undecanolide; 1,4-dodecanolide; 1,5-decanolide; 1,5-dodecanolide; 4-methyl-1,4-decanolide; 1,15-pentadecanolide; cis- and trans-11-pentadecen-1,15-olide; cis- and trans-12-pentadecen-1,15-olide; 1,16-hexadecanolide; 9-hexadecen-1,16-olide; 10-oxa-1,16-hexadecanolide; 11-oxa-1,16-hexadecanolide; 12-oxa-1,16-hexadecanolide; ethylene-1,12-dodecanedioate; ethylene-1,13-tridecanedioate; coumarin; 2,3-dihydrocoumarin; octahydrocoumarin.

Further preferred is a fragrance composition according to the invention as described above, wherein the proportion of the total amount of compound(s) of the formula (I) in the fragrance composition, based on the total weight of the fragrance composition, is 0.1 to 50% by weight, more preferably 0.5 to 15% by weight, particularly preferably 0.75 to 2% by weight.

Especially preferred is a fragrance composition according to the invention as described above, which contains one or more solvents as described above and according to a possible embodiment—preferably does not include any further fragrances, wherein the proportion of the total amount of compound(s) of the formula (I) in the fragrance composition, based on the total weight of the compound(s) of the formula (I) and of the solvent(s), is 0.1 to 50% by weight, more preferably 0.5 to 15% by weight, more preferably 0.75 to 2% by weight.

Furthermore, preferred is a fragrance composition according to the invention, wherein the fragrance composition comprises or consists of one or more compound(s) of formula (I)

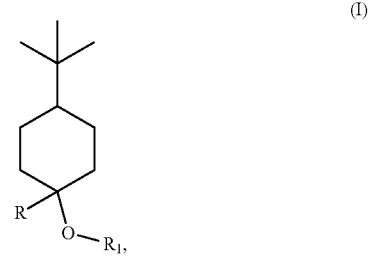

(I)

wherein R is methyl or ethyl and $R_1$ is H, methyl or ethyl,
preferably one or more compound(s) of formula (Ia) and/or (Ib) and/or (Ic),

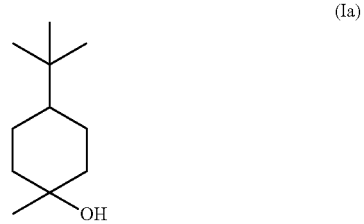

(Ia)

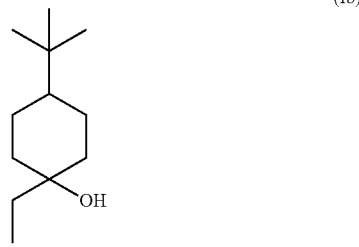

(Ib)

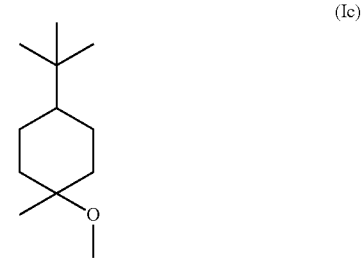

(Ic)

and
one or more solvents as described above,
and
one or more further fragrance(s),
wherein preferably the proportion of the total amount of compound(s) of the formula (I) and the total amount of further fragrance(s) in the fragrance composition, based on the total weight of the fragrance composition, is 0.1 to 50% by weight and/or wherein preferably the ratio of the total mass of the compound(s) of the formula (I) in the fragrance mixture to the total mass of further fragrance(s) in the fragrance mixture is in the range of from 1:90 to 1:5.

The fragrance compositions according to the invention preferably are perfume oils, perfumes, perfume extraits, eau de parfums, eau de toilettes, shaving lotions, eau de colognes, pre-shave products, splash colognes. The compound(s) of formula (I) to be used according to the invention thereby preferably form the top note of perfumes or perfume oils. The top note of a perfume oil includes those notes whose odour can be perceived particularly quickly.

A further aspect of the present invention relates to the use of a fragrance composition as described above for imparting, modifying and/or enhancing one or more olfactory notes selected from the group consisting of ambergris, indole and woody, preferably for rounding off, harmonizing and/or improving the natural olfactory impression of one or more further fragrance(s) and/or for imparting, modifying and/or enhancing an ambergris-like and/or woody and/or indol-like olfactory top note.

A further aspect of the present invention relates to a method for imparting, modifying and/or enhancing one or more olfactory notes selected from the group consisting of ambergris, indole and woody, preferably for rounding off, harmonizing and/or improving the natural olfactory impression of one or more further fragrance(s) and/or for imparting, modifying and/or enhancing an ambergris-like and/or woody and/or indole-like olfactory top note, comprising or consisting of the following steps:

(a) Providing (a.1) one or more compounds of formula (I)

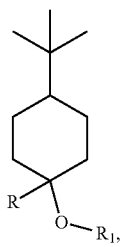

(I)

wherein R is methyl or ethyl and $R_1$ is H, methyl or ethyl, preferably one or more compound(s) of formula (Ia) and/or (Ib) and/or (Ic),

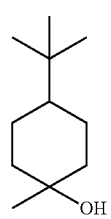

(Ia)

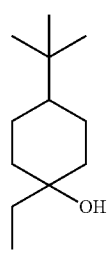

(Ib)

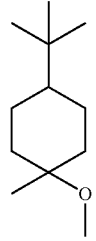

(Ic)

and (a.2) of one, two, three, four, five, six, seven, eight, nine, ten or more further fragrance(s), (b) adding the compound(s) of formula (I) (a.1) to the further fragrance(s) (a.2) in a sensorially effective amount, preferably in an amount sufficient to impart, enhance and/or modify one or more olfactory notes selected from the group consisting of ambergris, indole and woody, preferably in an amount sufficient to round off, harmonize and/or improve the natural olfactory impression of the one or more further fragrance(s) and/or to impart, enhance and/or modify an ambergris-like and/or woody and/or indol-like olfactory top note.

Another aspect of the present invention relates to a perfumed article comprising or consisting of (i) a fragrance composition according to the invention (as described herein)

or one or more compound(s) of formula (I)

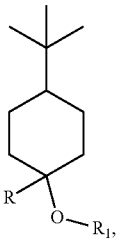

(I)

wherein R is methyl or ethyl and $R_1$ is H, methyl or ethyl, preferably one or more compound(s) of formula (Ia) and/or (Ib) and/or (Ic),

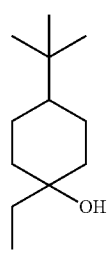

(Ic)

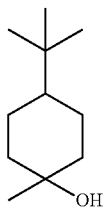
(Ia)

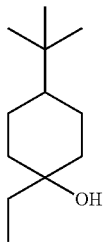
(Ib)

and optionally one or more solvent(s), preferably as described above, and/or one or more further fragrance(s), (ii) one or more further component(s), preferably at least one or more, preferably one, two, three, four, five or more, additive(s), excipient(s) and/or active substance(s).

The use of the compound(s) of formula (I) to be used according to the invention in the perfumed article according to the invention is particularly advantageous because of its/their low reactivity with other chemical compounds, so that neither the compound(s) of formula (I) to be used according to the invention nor the ingredients of the perfumed article according to the invention are adversely altered. In addition, the compound(s) of formula (I) to be used according to the invention in the concentrations necessary to obtain the desired scent effect does/do not adversely affect the physical or physicochemical properties of the perfumed articles according to the invention (e.g. their viscosity or pH value).

Preferred is a perfumed article according to the invention, wherein the article is selected from the group consisting of cosmetics, detergents and cleaning agents, fabric softeners, bleaching agents, disinfectants, fragrance release systems, sunscreens for the skin, hair care products, deodorants, acidic, alkaline and neutral cleaning agents, preferably floor cleaners, window glass cleaners, dishwashing detergents, bathroom and sanitary cleaners, scouring milk, solid and liquid WC cleaners, powdery and foamy carpet cleaners, liquid detergents, powdery detergents, laundry pre-treatments, bleaching agents, soaking agents, stain removers, fabric softeners, washing soaps, washing tablets, disinfectants, surface disinfectants, air fresheners in liquid, gel-like or on a solid carrier applied form including for scenting toilets, aerosol sprays, waxes, polishes, preferably furniture polishes, floor waxes, shoe creams, body care products, preferably solid and liquid soaps, shower gels, shampoos, shaving soaps, shaving foams, bath oils, cosmetic emulsions of the oil-in-water, water-in-oil and water-in-oil-in-water type, preferably skin creams and lotions, face creams and lotions, sun protection creams and lotions, after-sun creams and lotions, hand creams and lotions, foot creams and lotions, depilatory creams and lotions, after-shaves, after shave creams and lotions, pre-shaves, tanning creams and lotions, hair care products, preferably hair sprays, hair gels, hair lotions, hair conditioners, permanent and semi-permanent hair dyes, hair deformers such as cold waves and hair straightening agents, hair tonics, hair creams and lotions, refreshing tissues, deodorants, antiperspirants, preferably underarm sprays, roll-ons, deodorant sticks and creams and decorative cosmetic products, preferably make-up.

The additional ingredient(s) (ii) contained in the perfumed articles according to the invention, preferably the additive(s), excipient(s) and/or active substance(s) contained therein, are preferably preservatives, abrasives, anti-acne agents, anti-aging agents, antibacterial agents, anti-cellulite agents, anti-dandruff agents, anti-inflammatory agents, irritation preventing agents, irritation inhibiting agents, antimicrobial agents, antioxidants, astringents, antiperspirants, antiseptic agents, antistatic agents, binders, buffers, carrier materials, chelating agents, cell stimulants, cleansing agents, caring agents, depilatory agents, surface-active substances, deodorants, antiperspirants, softeners, emulsifiers, enzymes, essential oils, fibres, film-forming agents, fixers, foaming agents, foam stabilizers, foaming inhibitors, foam boosters, fungicides, gelling agents, gel-forming agents, hair care products, hair deformers, hair straightening agents, moisturizing agents, moistening substances, moist-keeping substances, bleaching agents, strengthening agents, stain-removing agents, optical brightening agents, impregnating agents, soil-repellent agents, friction-reducing agents, lubricants, moisturizing creams, ointments, opacifiers, plasticizing agents, covering agents, polish, brighteners, polymers, powders, proteins, refattening agents, abrasives, silicones, skin soothing agents, skin cleansing agents, skin caring agents, skin healing agents, skin brightening agents, skin protecting agents, skin softening agents, cooling agents, skin cooling agents, warming agents, skin warming agents, stabilizers, UV absorbing agents, UV filters, detergents, fabric softeners, suspending agents, skin tanning agents, thickening agents, vitamins, oils, waxes, fats, phospholipids, saturated fatty acids, mono- or polyunsaturated fatty acids, α-hydroxy acids, polyhydroxy fatty acids, plasticizers, dyes, colour protecting agents, pigments, anticorrosives, aromas, flavors, fragrances, polyols, surfactants, electrolytes, organic solvents or silicone derivatives. The compound(s) of formula (I) to be used in accordance with the invention preferably has/have a high compatibility with these substances.

In addition to the use as a liquid in solutions or in emulsions, the compound(s) of formula (I) to be used according to the invention or the fragrance composition according to the invention may be adsorbed on solids or may be used (micro)encapsulated in carriers. These dosage forms can provide both a fine distribution of the compound(s) of formula (I) or the fragrance composition in the product and a controlled release during application. Such solids may preferably be porous inorganic materials such as light sulphate, silica gels, zeolites, gypsums, clays, clay granules, gas concrete, etc. or organic materials such as woods, cellulose-based materials, sugar or plastics such as PVC, polyvinyl acetates or polyurethanes.

Encapsulation products may, for example, be spray-dried, be present as an inclusion complex or as an extrusion product. Microencapsulation of the compound(s) of formula (I) to be used according to the invention or of the perfume composition according to the invention may be effected, for example, by the so-called coacervation process with the aid of capsule materials, e.g. of polyurethane-like substances or soft gelatine.

The spray-dried compound(s) of formula (I) to be used according to the invention or the fragrance composition according to the invention may be prepared, for example, by spray-drying an emulsion or dispersion containing the compound(s) of formula (I) to be used according to the invention or the fragrance composition according to the invention, whereby modified starches, proteins, dextrin and vegetable gums may be used as carriers.

Inclusion complexes may be prepared, for example, by incorporating dispersions of the compound(s) of formula (I) to be used according to the invention or of the fragrance composition according to the invention and cyclodextrins or urea derivatives into a suitable solvent, e.g. water.

Extrusion products may be obtained by fusing the compound(s) of formula (I) to be used according to the invention or the fragrance composition according to the invention with a suitable waxy substance and by extrusion followed by solidification, if appropriate in a suitable solvent, e.g. isopropanol.

The adsorbates as well as the encapsulation products can be further optimized by so-called "coating" with suitable materials with regard to a more targeted release of scent, for which preferably wax-like plastics such as polyvinyl alcohol can be used.

Preferred is also a perfumed article according to the invention, wherein component (i) is contained in a sensorially effective amount, preferably in an amount sufficient for a consumer to perceive one or more olfactory notes selected from the group consisting of ambergris, indole and woody.

Further preferred is a perfumed article according to the invention, wherein the proportion of the total amount of compound(s) of formula (I), based on the total weight of the article, is in the range of from 0.0001 to 5% by weight, more preferably from 0.001 to 2% by weight, particularly preferably from 0.001 to 1% by weight.

According to another aspect, the present invention relates to a method for perfuming an article comprising or consisting of the following steps:

(a) Providing
  (a.1) a fragrance composition according to the invention (as described herein),
  or
  (a.2) one or more compound(s) of formula (I)

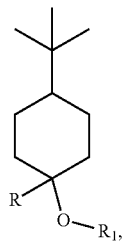

(I)

wherein R is methyl or ethyl and $R_1$ is H, methyl or ethyl,
preferably one or more compound(s) of formula (Ia) and/or (Ib) and/or (Ic),

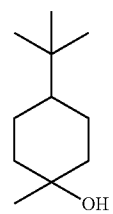

(Ia)

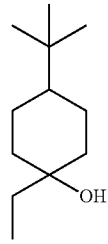

(Ib)

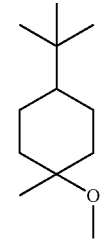

(Ic)

and optionally one or more solvent(s), preferably as described above, and/or one or more further fragrance(s), (b) adding the fragrance composition (a.1) or compound(s) of formula (I)/solvent (if present)/further fragrance(s) (if present) (a.2) to the article to be perfumed, in a sensorially effective amount, preferably in an amount sufficient to impart, enhance and/or modify one or more olfactory notes selected from the group consisting of ambergris, indole and woody, preferably in an amount sufficient to round off, harmonize and/or improve the natural olfactory impression of the one or more further fragrance(s) (if present), and/or to impart, enhance and/or modify an ambergris-like and/or woody and/or indole-like olfactory top note.

For preferred embodiments of this method, what has been stated above in connection with uses according to the invention or fragrance compositions according to the invention or articles according to the invention applies accordingly.

In the following, the invention is explained in more detail using selected examples. Unless otherwise stated, all data refer to the weight.

The compound(s) of formula (I) to be used according to the invention can be obtained, for example, by a Grignard reaction and, if applicable, subsequent etherification, starting from 4-tert.butylcyclohexanone, as shown below.

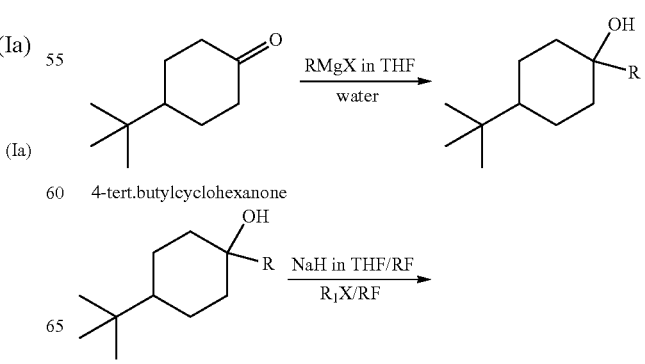

4-tert.butylcyclohexanone

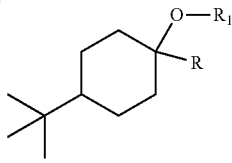

EXAMPLE 1

Synthesis of 4-tert-butyl-1-methyl-cyclohexanol Grignard Reaction 200 ml methyl magnesium chloride solution (3M in THF) and 100 ml THF are presented in an agitator with magnetic stirrer under a nitrogen atmosphere. Subsequently, 83.2 g (0.54 mol) of 4-tert.-butylcyclohexanone dissolved in 200 ml THF are added dropwise for 1 to 2 h at 20 to 25° C. The mixture is stirred further for 2 to 3 hours at RT. The batch is poured onto a cold, saturated ammonium chloride solution at 0 to 5° C., then extracted with MTBE and the organic phase is washed with soda solution and then with NaCl solution. After evaporation, 84.6 g of crude product is obtained.

The raw material is distilled in a small column.

Yield: 77.8 g (84.7% of theoretical yield)

EXAMPLE 2

Synthesis of 4-tert-butyl-1-methyl-cyclohexanol Methyl Ether Etherification

A solution of 42.5 g (0.25 mol) 4-tert-butyl-1-methyl-cyclohexanol in 100 ml absolute THF is added dropwise under a nitrogen atmosphere to 0.3 mol sodium hydride 60% in absolute THF at 20° C. in an agitator with magnetic stirrer. Then it is stirred for further 5 h at RF. Subsequently, 42.6 g (0.3 mol) methyl iodide in 100 ml absolute THF are added dropwise at RT within 30 minutes. Then it is stirred for another 2 hours at RT. The reaction mixture is carefully mixed with 250 ml ice-cold water under cooling and, after separation of the aqueous phase, washed again twice with 50 ml saturated saline solution, respectively, until neutral. After distilling off the solvent, the residue is distilled in a small column.

Yield: 28.8 g (62.8% of theoretical yield)

During manufacture of other compounds of formula (I) to be used according to the invention, the same excipients, equipment and parameters may be used.

EXAMPLES OF FRAGRANCE COMPOSITIONS ACCORDING TO THE INVENTION

Perfume Oil 1 Left: Comparison, Right: According to the Invention

| | | |
|---|---|---|
| AMBERWOOD ® F | 7.000 | 7.000 |
| AMBRETTOLIDE | 6.000 | 6.000 |
| Compound (Ia), (Ib) or (Ic) | 0.000 | 34.000 |
| BHT IONOL | 3.000 | 3.000 |
| CASSIS BASE 345 BB | 10.000 | 10.000 |
| CITRONELLOL 950 | 10.000 | 10.000 |
| CITRONELLYLACETATE EXTRA | 1.000 | 1.000 |
| DAMASCENONE 10% DPG | 5.000 | 5.000 |
| DAMASCONE ALPHA 10% DPG | 1.000 | 1.000 |
| DIPROPYLENE GLYCOL | 209.000 | 175.000 |
| ETHYLENE BRASSYLATE | 325.000 | 325.000 |
| GERANIOL SUPER | 20.000 | 20.000 |
| GERANYL ACETATE PURE | 1.000 | 1.000 |
| HEDIONE | 120.000 | 120.000 |
| HEDIONE HC/30 | 30.000 | 30.000 |
| HELIONAL | 4.000 | 4.000 |
| HEXENYL ACETATE CIS TRANS-3 10% DPG | 3.000 | 3.000 |
| HEXYL CINNAMIC ALDEHYDE ALPHA | 20.000 | 20.000 |
| HYDROXY CITRONELLAL | 15.000 | 15.000 |
| INDOL FF 10% DPG | 1.000 | 1.000 |
| IONONE BETA | 8.000 | 8.000 |
| ISO E SUPER | 100.000 | 100.000 |
| LEMON OIL WINTER BERGAPTEN FREE | 10.000 | 10.000 |
| LINALOOL | 5.000 | 5.000 |
| LINALYL ACETATE | 25.000 | 25.000 |
| MAGNOLAN | 20.000 | 20.000 |
| CLEMENTINE OIL DIST. DECOL. | 5.000 | 5.000 |
| METHYL IONONE GAMMA PURE/IFF | 1.000 | 1.000 |
| METHYL OCTINE CARBONATE 1% DPG | 5.000 | 5.000 |
| NEROL 900 | 2.000 | 2.000 |
| PHENYLETHYL ALCOHOL | 20.000 | 20.000 |
| ROSESSENCE 193E | 3.000 | 3.000 |
| VERTOCITRAL 10% DPG | 5.000 | 5.000 |

With the addition of compound (Ia) or (b) or (Ic), the perfume oil (right column) smells more harmonious, floral and natural and has a more intense ambergris note.

Perfume Oil 2 Left: Comparison, Right: According to the Invention

| | | |
|---|---|---|
| AMBRETTOLIDE | 15.000 | 15.000 |
| Compounds (Ia), (Ib) or (Ic) | 0.000 | 40.000 |
| BASIL OIL COMORES TYPE E 10% DPG | 2.000 | 2.000 |
| BERGAMOT OIL | 40.000 | 40.000 |
| BOURGEONAL 10% DPG | 5.000 | 5.000 |
| CARDAMOM OIL | 2.000 | 2.000 |
| CASHMERANE | 15.000 | 15.000 |
| CINNAMON BARK OIL CEYLON 10% DPG | 5.000 | 5.000 |
| MUSCATEL SAGE OIL | 2.000 | 2.000 |
| CORIANDER OIL | 3.000 | 3.000 |
| COUMARIN | 16.000 | 16.000 |
| DAMASCENONE | 2.000 | 2.000 |
| DIHYDRO MYRCENOL | 2.000 | 2.000 |
| DIPROPYLENE GLYCOL | 52.000 | 12.000 |
| FIR BALSAM ABS. 10% DPG | 5.000 | 5.000 |
| FLOROSA | 5.000 | 5.000 |
| GALAXOLIDE 50% IN DPG | 150.000 | 150.000 |
| GERANIOL SUPER | 3.000 | 3.000 |
| GERANYL ACETATE 60 | 2.000 | 2.000 |
| GLOBALIDE ® | 210.000 | 210.000 |
| GUAIAC WOOD OIL | 5.000 | 5.000 |
| HEDIONE | 30.000 | 30.000 |
| HEDIONE HC/30 | 60.000 | 60.000 |
| HEXENOL CIS-3 10% DPG | 5.000 | 5.000 |
| ISO E SUPER | 130.000 | 130.000 |
| ISOBUTYLCHINOLIN DL 100% 1% DPG | 5.000 | 5.000 |
| JAVANOL | 3.000 | 3.000 |
| LAVANDIN OIL ABRIALIS NAT. | 3.000 | 3.000 |
| LEMON OIL WINTER ITALY | 15.000 | 15.000 |
| LINALOOL | 15.000 | 15.000 |
| LINALYL ACETATE | 25.000 | 25.000 |
| METHYL IONONE GAMMA PUR/IFF | 3.000 | 3.000 |
| MUSCENONE | 4.000 | 4.000 |
| PATCHOULI OIL DECOL. | 5.000 | 5.000 |
| SANDALWOOD OIL EAST IND. 10% DPG | 5.000 | 5.000 |
| SANDRANOL ® | 10.000 | 10.000 |
| TONALIDE | 130.000 | 130.000 |
| VANILLIN | 3.000 | 3.000 |
| VERTOCITRAL 10% DPG | 5.000 | 5.000 |
| VETIVER OIL HAITI | 3.000 | 3.000 |

With the addition of compound (Ia) or (Ib) or (Ic), the perfume oil (right column) has besides a more intense ambergris note a greater floral radiance and appears more round and harmonious.

The invention claimed is:

1. A fragrance composition comprising:
one or more compounds of formula (I):

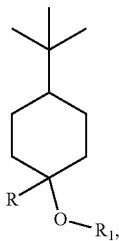

wherein R is methyl or ethyl and $R_1$ is H, methyl, or ethyl; and
and one or more solvents and/or one or more further fragrances.

2. The fragrance composition according to claim 1 comprising:
0.1 to 50% by weight of the one or more compounds of formula (I), based on the total weight of the fragrance composition.

3. The fragrance composition according to claim 1 comprising the one or more solvents and the one or more further fragrances.

4. The fragrance composition according to claim 1, wherein the one or more compounds of Formula (I) are selected from the group consisting of compounds of formula (Ia), formula (Ib), and formula (Ic):

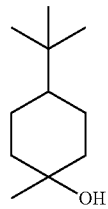

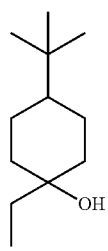

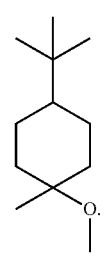

5. The fragrance composition according to claim 1 comprising the one or more solvents, wherein the one or more solvents are selected from the group consisting of ethanol, isopropanol, diethylene glycol monoethyl ether, glycerol, propylene glycol, 1,2-butylene glycol, dipropylene glycol, diethyl phthalate, triethyl citrate, and isopropyl myristate.

6. The fragrance composition according to claim 1 comprising the one or more further fragrances, wherein the weight ratio of a total amount of the one or more compounds of formula (I) to a total amount of the one or more further fragrances in the fragrance composition is 1:99 to 1:1.

7. A perfumed article comprising:
(i) a fragrance composition according to claim 1; and
(ii) one or more additives, excipients and/or active substances.

8. The perfumed article according to claim 7 selected from the group consisting of cosmetics, detergents and cleaning agents, fabric softeners, bleaching agents, disinfectants, fragrance release systems, sunscreens for the skin, hair care products, deodorants, acidic, alkaline and neutral cleaning agents, scouring milk, solid and liquid WC cleaners, powdery and foamy carpet cleaners, liquid detergents, powdery detergents, laundry pre-treatments, bleaching agents, soaking agents, stain removers, fabric softeners, washing soaps, washing tablets, disinfectants, surface disinfectants, air fresheners in liquid, gel-like or on a solid carrier applied form including for scenting toilets, aerosol sprays, waxes, polishes, floor waxes, shoe creams, body care products, solid and liquid soaps, shower gels, shampoos, shaving soaps, shaving foams, bath oils, cosmetic emulsions of the oil-in-water, water-in-oil and water-in-oil-in-water type, skin creams and lotions, face creams and lotions, sun protection creams and lotions, after-sun creams and lotions, hand creams and lotions, foot creams and lotions, depilatory creams and lotions, after-shaves, after shave creams and lotions, pre-shaves, tanning creams and lotions, hair care products, hair sprays, hair gels, hair lotions, hair conditioners, permanent and semi-permanent hair dyes, hair deformers such as cold waves and hair straightening agents, hair tonics, hair creams and lotions, refreshing tissues, deodorants, antiperspirants, underarm sprays, roll-ons, deodorant sticks and creams and decorative cosmetic products.

9. The perfumed article according to claim 7, wherein the one or more compounds of formula (I) are in an amount sufficient for a consumer to perceive one or more olfactory notes selected from the group consisting of ambergris, indole, and woody.

10. The perfumed article according to claim 7 comprising 0.0001 to 5% by weight of the one or more compounds of formula (I), based on the total weight of the article.

11. A method for perfuming a composition comprising incorporating a sensorially effective amount of one or more compounds of formula (I) into the composition:

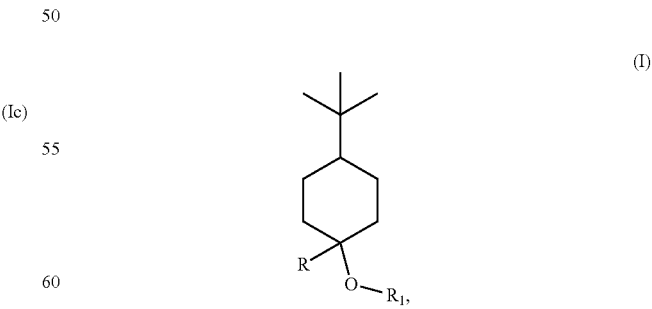

wherein R is methyl or ethyl and $R_1$ is H, methyl, or ethyl.

12. The method according to claim 11, wherein the composition comprises one or more solvents and/or one or more further fragrances that are not compounds of formula (I).

13. The method according to claim 11, wherein the one or more compounds of formula (I) are selected from from the group consisting of compounds of formula (Ia), formula (Ib), and formula (Ic):

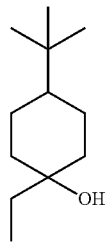

(Ia)

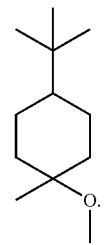

(Ib)

(Ic)

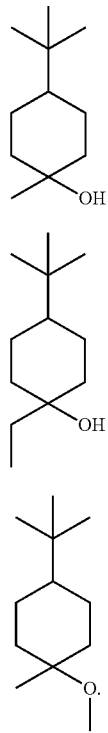

14. The method according to claim 11, wherein the method imparts, modifies, and/or enhances one or more olfactory notes selected from the group consisting of ambergris, indole, and woody.

15. The method according to claim 11, wherein the composition is an article and the article comprises one or more additives, excipients and/or active substances.

16. The method according to claim 15, wherein the one or more compounds of formula (I) are in an amount sufficient for a consumer to perceive one or more olfactory notes selected from the group consisting of ambergris, indole, and woody.

17. The method according to claim 15, wherein 0.0001 to 5% by weight of the one or more compounds of formula (I) are incorporated into the article, based on the total weight of the article.

18. The method according to claim 15, wherein the one or more compounds of formula (I) are selected from from the group consisting of compounds of formula (Ia), formula (Ib), and formula (Ic):

(Ia)

-continued (Ib)

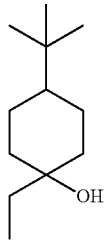

(Ic)

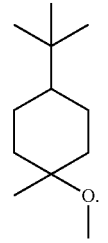

19. The method according to claim 15, wherein the article is selected from the group consisting of cosmetics, detergents and cleaning agents, fabric softeners, bleaching agents, disinfectants, fragrance release systems, sunscreens for the skin, hair care products, deodorants, acidic, alkaline and neutral cleaning agents, scouring milk, solid and liquid WC cleaners, powdery and foamy carpet cleaners, liquid detergents, powdery detergents, laundry pre-treatments, bleaching agents, soaking agents, stain removers, fabric softeners, washing soaps, washing tablets, disinfectants, surface disinfectants, air fresheners in liquid, gel-like or on a solid carrier applied form including for scenting toilets, aerosol sprays, waxes, polishes, floor waxes, shoe creams, body care products, solid and liquid soaps, shower gels, shampoos, shaving soaps, shaving foams, bath oils, cosmetic emulsions of the oil-in-water, water-in-oil and water-in-oil-in-water type, skin creams and lotions, face creams and lotions, sun protection creams and lotions, after-sun creams and lotions, hand creams and lotions, foot creams and lotions, depilatory creams and lotions, after-shaves, after shave creams and lotions, pre-shaves, tanning creams and lotions, hair care products, hair sprays, hair gels, hair lotions, hair conditioners, permanent and semi-permanent hair dyes, hair deformers such as cold waves and hair straightening agents, hair tonics, hair creams and lotions, refreshing tissues, deodorants, antiperspirants, underarm sprays, roll-ons, deodorant sticks and creams and decorative cosmetic products.

20. The fragrance composition according to claim 1, wherein R is methyl or ethyl and $R_1$ is methyl or ethyl.

21. The fragrance composition according to claim 1, wherein the one or more compounds of Formula (I) includes the compound of formula (Ia):

(Ia)

22. The fragrance composition according to claim 1, wherein the one or more compounds of Formula (I) includes the compound of formula (Ib):
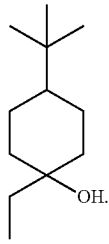
(Ib)
23. The fragrance composition according to claim 1, wherein the one or more compounds of Formula (I) includes the compound of formula (Ic):
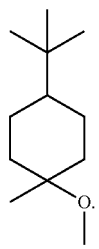
(Ic)
* * * * *